United States Patent
Govari et al.

(10) Patent No.: US 12,144,635 B2
(45) Date of Patent: Nov. 19, 2024

(54) SOLVING DOUBLE POTENTIAL PROBLEMS

(71) Applicant: BIOSENSE WEBSTER (ISRAEL) LTD., Yokneam (IL)

(72) Inventors: Assaf Govari, Haifa (IL); Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 113 days.

(21) Appl. No.: 16/718,391

(22) Filed: Dec. 18, 2019

(65) Prior Publication Data

US 2021/0186349 A1 Jun. 24, 2021

(51) Int. Cl.
| | |
|---|---|
| A61B 5/00 | (2006.01) |
| A61B 5/339 | (2021.01) |
| A61B 5/349 | (2021.01) |
| A61B 18/00 | (2006.01) |
| A61B 18/12 | (2006.01) |
| A61M 25/01 | (2006.01) |

(52) U.S. Cl.
CPC .............. *A61B 5/349* (2021.01); *A61B 5/339* (2021.01); *A61B 5/7475* (2013.01); *A61B 2018/00351* (2013.01); *A61B 2018/00577* (2013.01); *A61B 2018/00839* (2013.01); *A61B 18/1206* (2013.01); *A61M 25/0127* (2013.01)

(58) Field of Classification Search
CPC ........ A61B 5/349; A61B 5/339; A61B 5/7475
See application file for complete search history.

(56) References Cited

U.S. PATENT DOCUMENTS

| | | | |
|---|---|---|---|
| 6,236,883 B1 | 5/2001 | Ciaccio | |
| 6,690,963 B2 | 2/2004 | Ben Haim | |
| 8,948,837 B2 * | 2/2015 | Harlev | A61B 5/7285 600/374 |

(Continued)

OTHER PUBLICATIONS

European Search Report for corresponding EPA No. 20214909.2 dated Apr. 30, 2021.

(Continued)

*Primary Examiner* — Sana Sahand
(74) *Attorney, Agent, or Firm* — Dergosits & Noah LLP; Todd A. Noah (57) ABSTRACT

A method and apparatus for electrophysiological assessment, including acquiring electrical signals from tissue at locations in a heart chamber and a computer processor automatically deriving from the electrical signals annotations indicative of times within a heart cycle at which a conduction wave traversed the locations. The method includes receiving an input from a processor user indicating, for a first location in the tissue where the electrical signals include a double-potential signal, a first annotation as a valid annotation. The processor automatically identifies second locations, within a predefined distance from the first location, where the electrical signals include double-potential signals, each having two respective annotations. The method further includes the processor automatically selecting, in response to the selection of the first annotation, one of the two respective annotations as the valid annotation at each of the second locations and displaying the valid annotations on an electroanatomical map of the heart.

22 Claims, 6 Drawing Sheets

(56) References Cited

U.S. PATENT DOCUMENTS

| | | | |
|---|---|---|---|
| 9,888,862 B2* | 2/2018 | Harlev | A61B 5/743 |
| 10,314,542 B2 | 6/2019 | Bar-Tal | |
| 10,335,052 B2 | 7/2019 | El Haddad | |
| 2008/0194979 A1 | 8/2008 | Madry | |
| 2012/0184863 A1 | 7/2012 | Harlev | |
| 2012/0184865 A1* | 7/2012 | Harlev | A61B 18/00 |
| | | | 600/509 |
| 2017/0079539 A1 | 3/2017 | Chauhan | |
| 2018/0189969 A1* | 7/2018 | Bustan | G06T 19/20 |
| 2018/0235495 A1 | 8/2018 | Rubenstein | |
| 2018/0296108 A1* | 10/2018 | Stewart | A61B 34/25 |
| 2018/0296167 A1 | 10/2018 | Stewart | |

OTHER PUBLICATIONS

Raymond W. Sy, "Modern Electrophysiology Mapping Techniques", Heart, Lung and Circulation 2012; 21: 364-375.

Tobias Georg Oesterlein et al., "Analysis and visualization of intracardiac electrograms in diagnosis and research: Concept and application of KaPAVIE", Computer Methods and Programs in Biomedicine, 127 (2016) 165-173.

\* cited by examiner

SOLVING DOUBLE POTENTIAL PROBLEMS

FIELD OF THE INVENTION

The present invention relates generally to analyzing results of a cardiac invasive procedure, and specifically to correcting erroneous results.

BACKGROUND OF THE INVENTION

An invasive cardiac procedure typically includes acquiring intra-cardiac (IC) electrocardiograph (ECG) signals, and analyzing the signals. Analysis of IC ECG signals is well known in the art.

For example, U.S. Pat. No. 10,314,542 to Bar-Tal et al. describes a system for determining regions of interest for heart ablation using fractionation. The method can comprise detecting, via sensors, electro-cardiogram (ECG) signals, each ECG signal detected via one of the sensors and indicating electrical activity of a heart. The system also includes determining regions of interest for heart ablation in accordance with the fractionation.

U.S. Patent Application No. 2018/0235495 to Rubenstein describes cardiac mapping catheters and methods for using the catheters. A catheter can detect the presence, direction and/or source of a depolarization wave front associated with cardiac arrhythmia.

U.S. Pat. No. 10,335,052 to El Haddad describes a device for analyzing electrophysiological data. The device generates a signal indicative for a presence of a pulmonary vein potential component using processing means adapted for performing a stepwise analysis of the electrophysiological data.

U.S. Pat. No. 6,236,883 to Ciaccio et al. describes a method comprising the steps of identifying and localizing reentrant circuits from electrogram features using feature detection and localization (FDL) algorithms.

U.S. Patent Application No. 2017/0079539 to Chauhan et al. describes a system for identifying focal source locations of electrophysiological activity in an organ. The system may also be used to guide catheter ablation of the organ.

SUMMARY OF THE INVENTION

An exemplary embodiment of the present invention provides a method for electrophysiological assessment, including:
acquiring electrical signals from myocardial tissue at multiple locations in a chamber of a heart;
automatically deriving from the electrical signals, by a computer processor, respective annotations, which are indicative of times within a cycle of the heart at which a conduction wave in the myocardial tissue traversed the locations;
receiving an input from a user of the computer processor indicating, for a first location in the tissue where the electrical signals include a double-potential signal having a first annotation and a second annotation at different respective times within the cycle of the heart, a selection of the first annotation as a valid annotation;
automatically identifying, by the computer processor, one or more second locations, within a predefined distance from the first location, where the electrical signals include double-potential signals, each having two respective annotations;
automatically selecting, by the computer processor, in response to the selection of the first annotation, one of the two respective annotations as the valid annotation at each of the one or more second locations; and
displaying the valid annotations on an electroanatomical map of the heart.

In a disclosed exemplary embodiment the chamber includes an atrium of the heart.

In a further disclosed exemplary embodiment the chamber includes a ventricle of the heart.

In a yet further disclosed exemplary embodiment the respective annotations include respective maximum voltages of a P-wave of the heart. Alternatively or additionally, the respective annotations include respective most negative $$\frac{dV}{dt}s$$

of a P-wave of the heart.

In an alternative exemplary embodiment the respective annotations include respective steepest negative slopes of a QRS complex of the heart.

In a further alternative exemplary embodiment, prior to the selection of the first annotation as the valid annotation by the user, the computer processor provides an indication to the user that the first annotation is the valid annotation.

In a yet further alternative exemplary embodiment, prior to the selection of the first annotation as the valid annotation by the user, the computer processor provides an indication to the user that the second annotation is the valid annotation.

In another exemplary embodiment, prior to the selection of the first annotation as the valid annotation by the user, for a given second location the computer processor selects the one of the two respective annotations as an invalid annotation.

In yet another exemplary embodiment, prior to the selection of the first annotation as the valid annotation by the user, for a given second location the computer processor selects the one of the two respective annotations as the valid annotation.

Displaying the valid annotations may include calculating respective local activation times (LATs) for the first location and the one or more second locations, and incorporating the LATs into the electroanatomical map of the heart.

There is also provided, in another exemplary embodiment of the present invention, apparatus for electrophysiological assessment, including:
a probe configured to acquire electrical signals from myocardial tissue at multiple locations in a chamber of a heart; and
a computer processor configured to:
automatically derive from the electrical signals, respective annotations, which are indicative of times within a cycle of the heart at which a conduction wave in the myocardial tissue traversed the locations,
receive an input from a user of the computer processor indicating, for a first location in the tissue where the electrical signals include a double-potential signal having a first annotation and a second annotation at different respective times within the cycle of the heart, a selection of the first annotation as a valid annotation,
automatically identify, one or more second locations, within a predefined distance from the first location, where the electrical signals include double-potential signals, each having two respective annotations, automatically select, in response to the selection of the first annotation, one of the two respective annotations as the valid annotation at each of the one or more second locations, and display the valid annotations on an electroanatomical map of the heart.

BRIEF DESCRIPTION OF THE DRAWINGS

The present disclosure will be more fully understood from the following detailed description of the exemplary embodiments thereof, taken together with the drawings, in which.

DETAILED DESCRIPTION OF EMBODIMENTS

Overview

An electroanatomical map of a chamber of a heart may be used by a physician to formulate an electrophysiological assessment of the chamber. The map comprises superimposed values of local activation times (LATs) on locations of a three-dimensional (3D) map of the heart chamber. (The superposition is typically by coloring the 3D map.) The LATs correspond to times at which a conduction wave in the tissue of the chamber traverses the locations.

A computer processor typically calculates the LATs from annotations of intra-cardiac electrocardiograph (IC ECG) signals, and the processor may calculate the annotation for a given signal automatically. For example, the annotation for an IC ECG signal from an atrium of the heart may be set as the maximum of the P-wave of the signal, and the annotation for an IC ECG signal from a ventricle may be set at the point of steepest negative slope of a QRS complex However, the processor may set the annotations incorrectly. For example, in the case of the atrium the P-wave may have two maxima, i.e., be a double-potential signal, and the processor may select the wrong maximum as the signal annotation.

Exemplary embodiments of the present invention enable a user of the processor to correct an invalid annotation of a double-potential signal for a given location. The processor then automatically propagates the effect of the correction to neighboring locations in a zone surrounding the user-selected given location, by checking and automatically correcting, if necessary, annotations of double-potential signals in the neighboring locations.

Thus, in an embodiment of the present invention, electrical signals from myocardial tissue at multiple locations in a chamber of a heart are acquired. A computer processor then automatically derives from the signals respective annotations, which are indicative of times within a cycle of the heart at which a conduction wave in the tissue traverses the locations.

A user of the processor provides an input to the processor, for a selected double-potential signal, that indicates which of two annotations of the signal is valid. The processor then automatically identifies locations, within a predefined distance of the location of the selected signal, that have double-potential signals.

For each of the automatically identified locations the processor automatically selects one of the two annotations as the valid annotation for the location. The automatic selection is in response to the user selected annotation referred to above. For example, for a given automatically identified location, the processor may choose the annotation that is closest in time to the user selected annotation to be the valid annotation of the identified location.

The valid annotations are then incorporated into an electroanatomical map of the heart, typically by using the annotations to compute corresponding LATs that are superimposed on a 3D map of the heart.

System Description

In the following description, like elements in the drawings are identified by like numerals, and like elements are differentiated as necessary by appending a letter to the identifying numeral.

Figure 1:
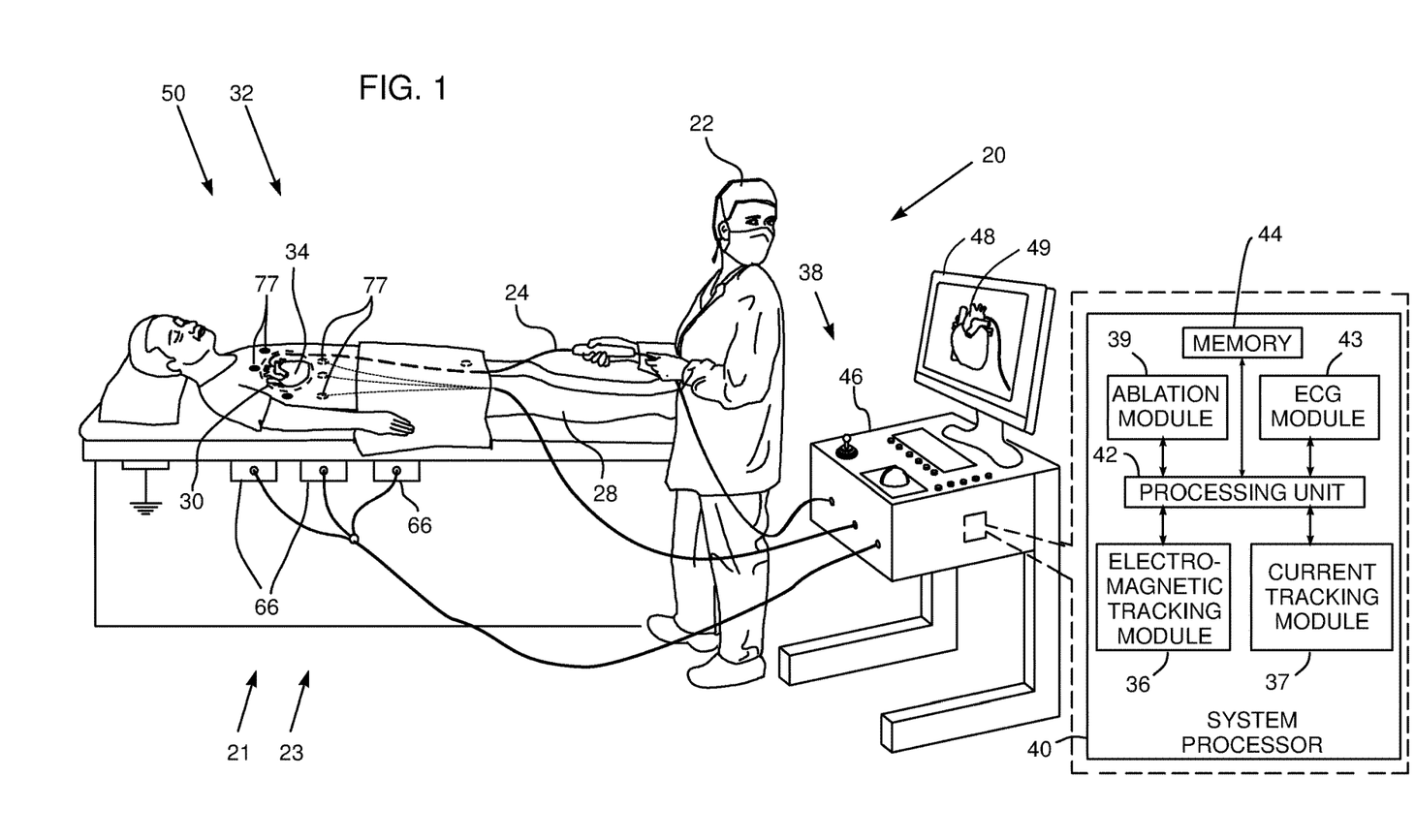
FIG. 1 is a schematic illustration of a double potential analysis system, according to an exemplary embodiment of the present invention.
Figure 2:
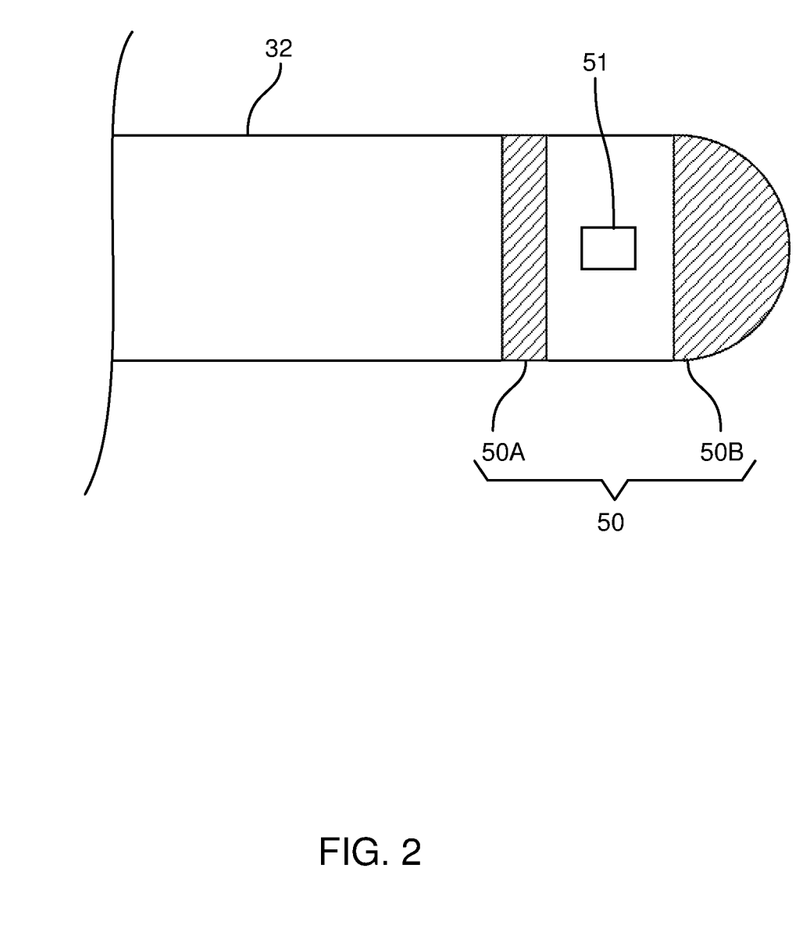
FIG. 2 is a schematic illustration of a distal end of a catheter used in the system, according to an exemplary embodiment of the present invention.

Reference is now made to FIG. 1, which is a schematic illustration of a double potential analysis system 20, and to FIG. 2, which is a schematic illustration of a distal end of a catheter used in the system, according to an embodiment of the present invention. For simplicity and clarity, the following description, except where otherwise stated, assumes a medical procedure is performed by a user 22 of system 20, herein assumed to be a medical practitioner, wherein the user inserts a catheter 24 into a left or right femoral vein of a patient 28. User 22 is also referred to herein as operator 22. The procedure is assumed to comprise investigation of a chamber of a heart 34 of the patient, and in the procedure, the catheter is initially inserted into the patient until a distal end 32 of the catheter, also herein termed probe 32, reaches the heart chamber. The chamber typically comprises an atrium or a ventricle of the heart.

System 20 may be controlled by a system processor 40, comprising a processing unit (PU) 42 communicating with an electromagnetic tracking module 36 and/or a current tracking module 37. PU 42 also communicates with an ablation module 39 and an ECG (electrocardiograph) module 43. The functions of the modules are described in more detail below. PU 42 also communicates with a memory 44. Processor 40 is typically mounted in a console 46, which comprises operating controls 38, typically including a pointing device such as a mouse or trackball, that operator 22 uses to interact with the processor. The processor uses software stored in memory 44 to operate system 20. Results of the operations performed by processor 40 are presented to the operator on a display 48. The results, which are typically in the form of an electroanatomical map 49 of heart 34, enable the operator to form an electrophysiological assessment of the heart. The software may be downloaded to processor 40 in electronic form, over a network, for example, or it may, alternatively or additionally, be provided and/or stored on non-transitory tangible media, such as magnetic, optical, or electronic memory.

For tracking the path of probe 32 in a mapping region 30 containing heart 34, embodiments of the present invention use at least one of a current based tracking system 21 and an electromagnetic based tracking system 23. Both systems are described below.

Tracking system 21 comprises a current measuring tracking system, similar to that described in U.S. Pat. No. 8,456,182 to Bar-Tal et al., whose disclosure is incorporated herein by reference. The Carto® system produced by Biosense-Webster of 33 Technology Drive, Irvine, Calif. 92618 USA, also uses a current measuring tracking system. The current measuring tracking system is under control of current tracking module 37. Probe 32 has one or more probe electrodes 50, herein by way of example assumed to comprise an electrode 50A and an electrode 50B, and in tracking system 21 module 37 injects currents to the one or more electrodes 50 being tracked. The currents are received, by a plurality of generally similar patch electrodes 77, also herein termed patches, which are positioned on the skin of patient 28, and transferred back to the module.

While conductive cabling to patch electrodes 77 and for other skin electrodes described herein is present for each of the electrodes, for clarity cabling is only shown in the figure for some of the electrodes. The currents between a given probe electrode 50 and skin patches 77 vary according to the location of the electrode, because, inter alia, of the different distances of the electrode from the patches, which cause different impedances between the given probe electrode and the different patches. Module 37 measures the different currents received by the different patches 77 on respective channels connected to the patches, and may be configured to generate an indication of the location of the given probe electrode from the different currents.

Electromagnetic tracking system 23 is similar to that described in U.S. Pat. No. 6,690,963 to Ben-Haim et al., whose disclosure is incorporated herein by reference, and to that used in the Carto® system. The electromagnetic tracking system is under control of electromagnetic tracking module 36. The electromagnetic tracking system comprises a plurality of magnetic field generators, herein assumed to comprise three sets of generators 66, each set comprising three orthogonal coils, so that the plurality of generators comprises a total of nine coils. Generators 66 are placed in known locations beneath patient 28, the known locations defining a frame of reference of the generators. Module 36 controls, inter alia, the amplitude and frequency of the alternating magnetic fields produced by the generators.

The alternating magnetic fields interact with a coil 51 located in probe 32, so as to generate alternating electropotentials in the coil, and the electropotentials are received as a signal by tracking module 36. The module, together with processing unit 42, analyzes the received signal, and from the analysis is able to determine a position, i.e., a location and an orientation, of the probe coil in the defined frame of reference.

Typically the tracking by either or both of the systems may be presented visually on display 48, for example by incorporating an icon representing the probe into map 49 of heart 34, as well as a path taken by the icon. For clarity, in the following description, only electromagnetic tracking system 23 is assumed to be used, but the description may be adapted, *mutatis mutandis*, for cases where both system 23 and system 21 are used, or if only system 21 is used.

Ablation module 39 comprises a radiofrequency (RF) generator which delivers RF power to a region of heart 34 that is selected by operator 22, so as to ablate the region. Operator 22 selects the region by positioning an ablation probe, with an ablation electrode, at the region. In some embodiments probe 32 and one of electrodes 50, such as electrode 50B, may be used as an ablation probe and an ablation electrode. Alternatively a separate ablation probe and ablation electrode may be used for the ablation provided by module 39.

ECG module 43 receives intra-cardiac (IC) ECG signals acquired by electrodes 50 when the electrodes are in contact with myocardial tissue of a chamber of heart 34. The ECG module together with PU 42 analyzes the signals, as described below, to find, inter alia, local activation times (LATs) of the signals. The module typically formulates its LAT measurements relative to a reference ECG signal, such as may be provided by an electrode positioned in the coronary sinus of heart 34.

Figure 3:
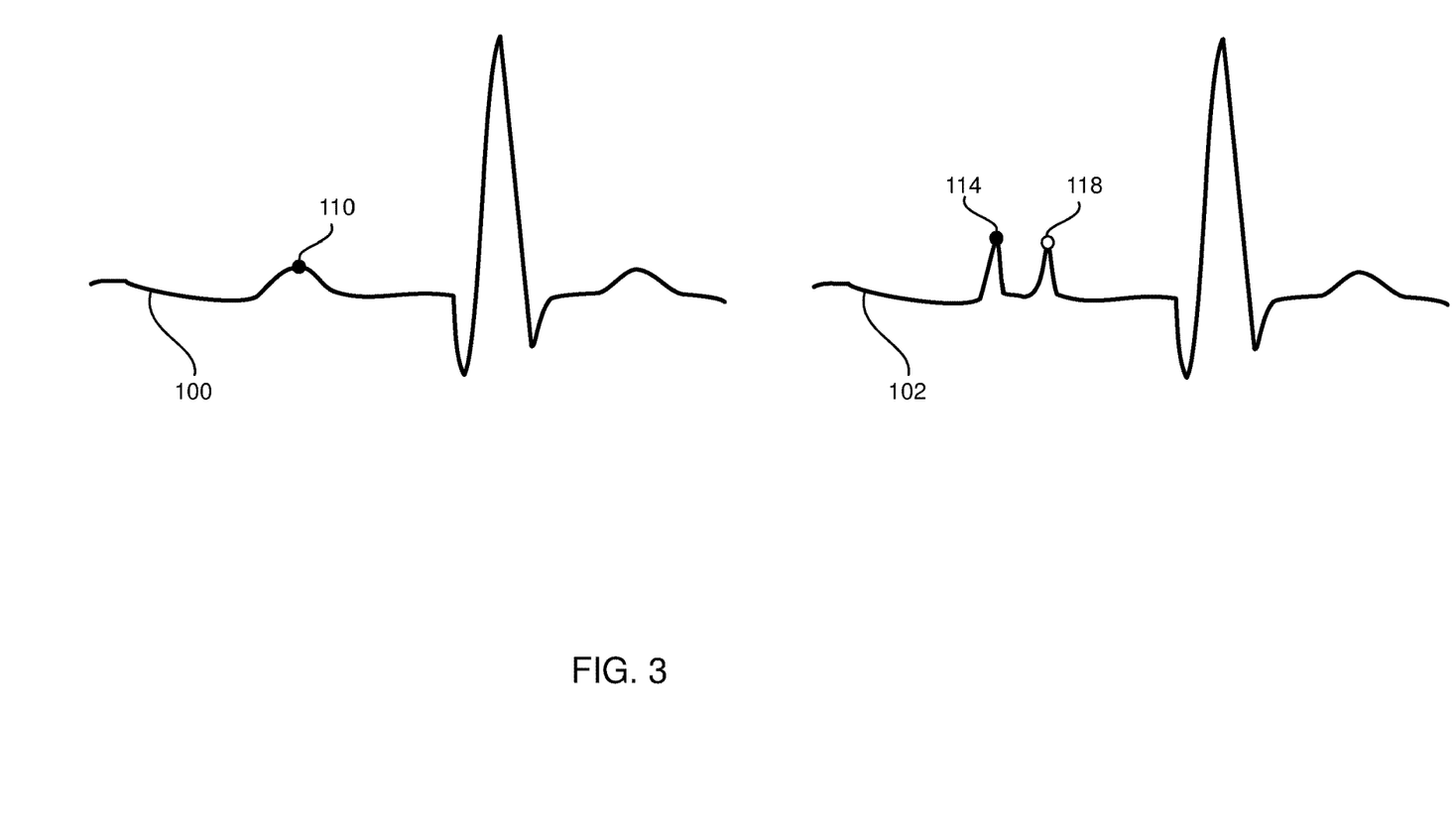
FIG. 3 shows examples of intra-cardiac electrocardiograph signals, according to an exemplary embodiment of the present invention.

FIG. 3 shows examples of IC ECG signals, according to an embodiment of the present invention. Signals 100 and 102 are acquired by electrodes 50 in contact with respective locations of the myocardial tissue of the heart chamber, herein by way of example assumed to be an atrium. The signals are voltage vs. time signals, and for simplicity axes for the signals are not illustrated in FIG. 3. PU 42 and module 43 analyze each signal to determine one or more annotations of each of the signals. An annotation for a given location is indicative of a time, the LAT, in the cycle of the beating heart at which a conduction wave in the heart traverses the location, and is assumed herein to comprise an ordered pair of the signal, i.e., a voltage V and a time t of the signal.

As is known in the art, the annotation for a given ECG signal may be set by different methods. For example, the annotation for a ventricle may be selected to be at a point on the QRS complex wherein the negative slope is steepest, i.e., wherein $$\frac{dV}{dt}$$

is most negative. For an atrium the annotation may be set at the maximum of the P-wave of the signal, or alternatively at the time where $$\frac{dV}{dt}$$

of the P-wave is most negative.

In the following description, except where otherwise stated, IC ECG signals are assumed to be acquired from an atrium of the heart, and the annotation for the acquired signals is assumed to be at the time of the maximum of the P-wave signal. Cases where the annotation of the P-wave is at the time where $$\frac{dV}{dt}$$

is most negative are noted further below.

Signal 100 illustrates a signal having a single annotation 110, at the peak of the P-wave, and such signals are also termed single potential signals. Signals having a single annotation, such as signal 100, are typically generated by heart 34 when it is beating in sinus rhythm.

Signal 102 illustrates a signal having two annotations 114, 118, wherein the P-wave has two peaks, and such signals are termed double-potential signals. While a heart beating in sinus rhythm may generate double-potential signals, the presence of double potentials may be indicative of, for example, an arrhythmia, scar tissue, or ablated tissue.

As explained below, signals such as those illustrated in FIG. 3 are used to produce electroanatomical map 49 of heart 34.

Figure 4:
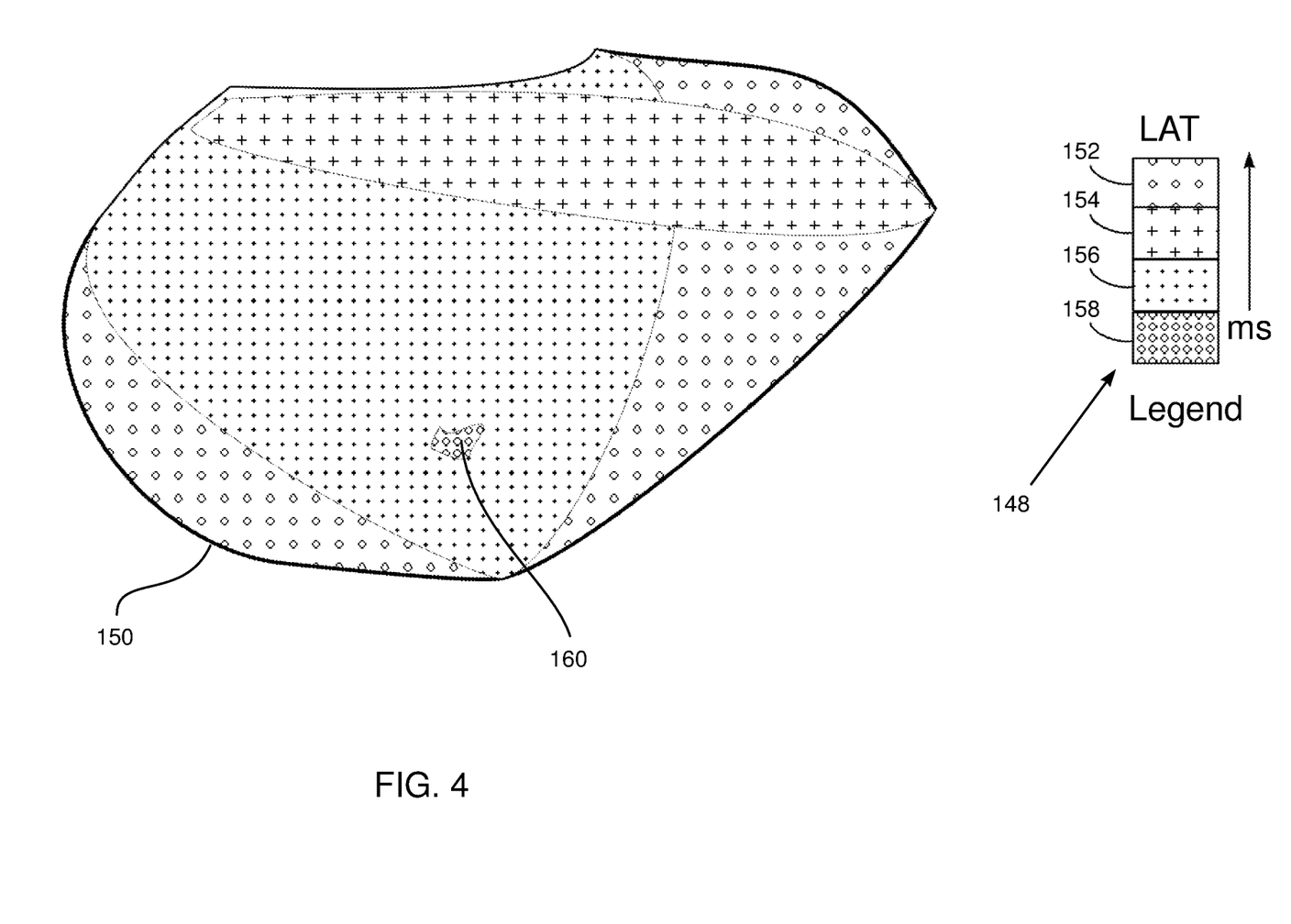
FIG. 4 is a schematic illustration of an electroanatomical map of a section of an atrium of a heart, according to an exemplary embodiment of the present invention.

FIG. 4 is a schematic illustration of an electroanatomical map 150 of a section of an atrium of heart 34, according to an embodiment of the present invention. Map 150 illustrates a portion of electroanatomical map 49.

To produce map 49, a three-dimensional (3D) map of the atrium may be first generated, by moving distal end 32 within the atrium, and tracking and recording positions of the distal end using one of the tracking systems referred to above. The recorded positions comprise a point cloud of positions within and at a surface of the atrium, and processor 40 may then analyze the point cloud, by methods which are well known in the art, to produce a 3D envelope enclosing the point cloud, the envelope corresponding to the tissue surface of the atrium.

Once the 3D map has been produced, the surface of the atrium may be characterized by acquiring and recording IC ECG signals from locations on the surface of the atrium. The signal acquisition may be performed using electrodes 50 of distal end 32, while recording the location of the distal end, and thus of the electrodes. The characterization may be as illustrated above for the signals of FIG. 3, comprising processor 40 calculating annotations for the signals. From the annotations the processor may initially assign LATs to the locations where the IC ECG signals are acquired, by methods which are well known in the art.

For single potential signals the LAT typically corresponds to the time of the single potential annotation, i.e., the time of the P-wave maximum. Thus, for signal 100, the LAT is at the time of annotation 110. For double potential signals the LAT, except as described further below, is assumed to correspond to the time of the annotation having the largest voltage. (If the annotation is defined in terms of the $$\frac{dV}{dt}$$

of the signal, the LAT is assumed to correspond to the time of the annotation having the most negative $$\frac{dV}{dt}.)$$

Thus, for signal 102, if annotation 114 has a larger voltage than annotation 118, the LAT is at the time of annotation 114. In displays of the annotated signals, referred to further below, typically only the annotation selected for the LAT is superimposed on signals. In FIG. 3 annotation 114 has been drawn as a filled circle to indicate it is the annotation that has been selected for the LAT of signal 102. Similarly, annotation 110 has been drawn as a filled circle to indicate it is the annotation that has been selected for the LAT of signal 100.

Once the LAT values for specific locations have been determined, the processor may overlay the measured values on the 3D map of the chamber, typically interpolating between the values, to produce an electroanatomical map. The different LAT values are typically illustrated in maps 150 and 49 as different colors, but are shown schematically in FIG. 4 as different types of shading 152, 154, 156, 158.

The values, typically in ms, of the LATs may be shown on display 48 as a legend 148 for the map, as is schematically illustrated in FIG. 4.

Operator 22 may review map 150, and from the review may decide to check an area of the map, typically because the LAT of the chamber location, corresponding to the map area, may appear to be incorrect. For example, operator 22 may check if an area 160 on map 150 is correctly characterized, i.e., has a correct LAT.

To check if the assigned LAT of a location is correct, operator 22 inspects the relevant IC ECG signals acquired by electrodes 50 from the location. Alternatively or additionally, typically in the case that the LAT of the location is derived from interpolation, the operator inspects IC ECG signals acquired from regions of the atrium close to the location.

An algorithm comprising steps involved in the review and inspection of map 150 is described in detail below, with respect to FIGS. 5A and 5B.

Figure 5A:
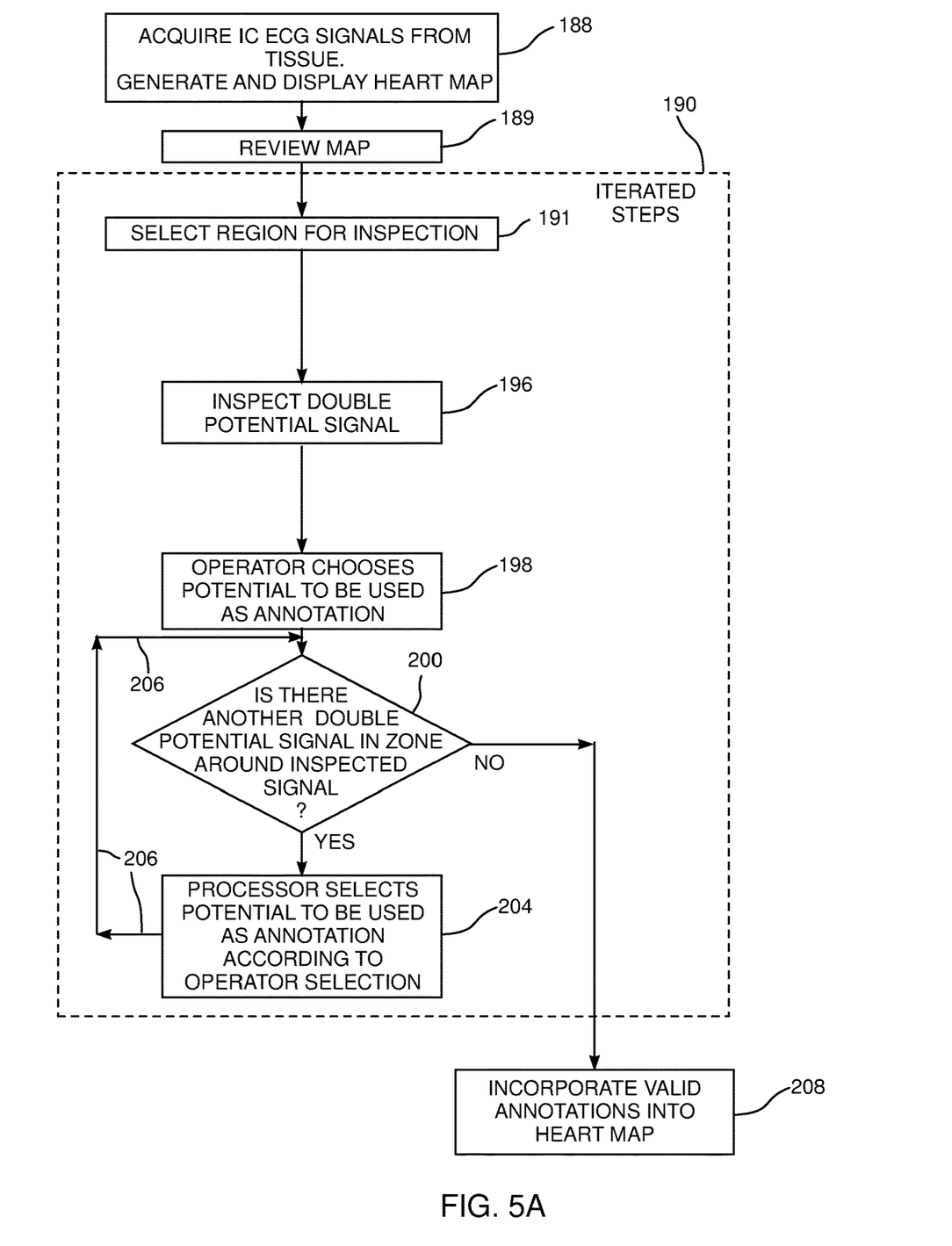
FIG. 5A is a flowchart of steps of an algorithm and FIG. 5B is a schematic illustration of a map explaining some of the steps, according to an exemplary embodiment of the present invention.
Figure 5B:
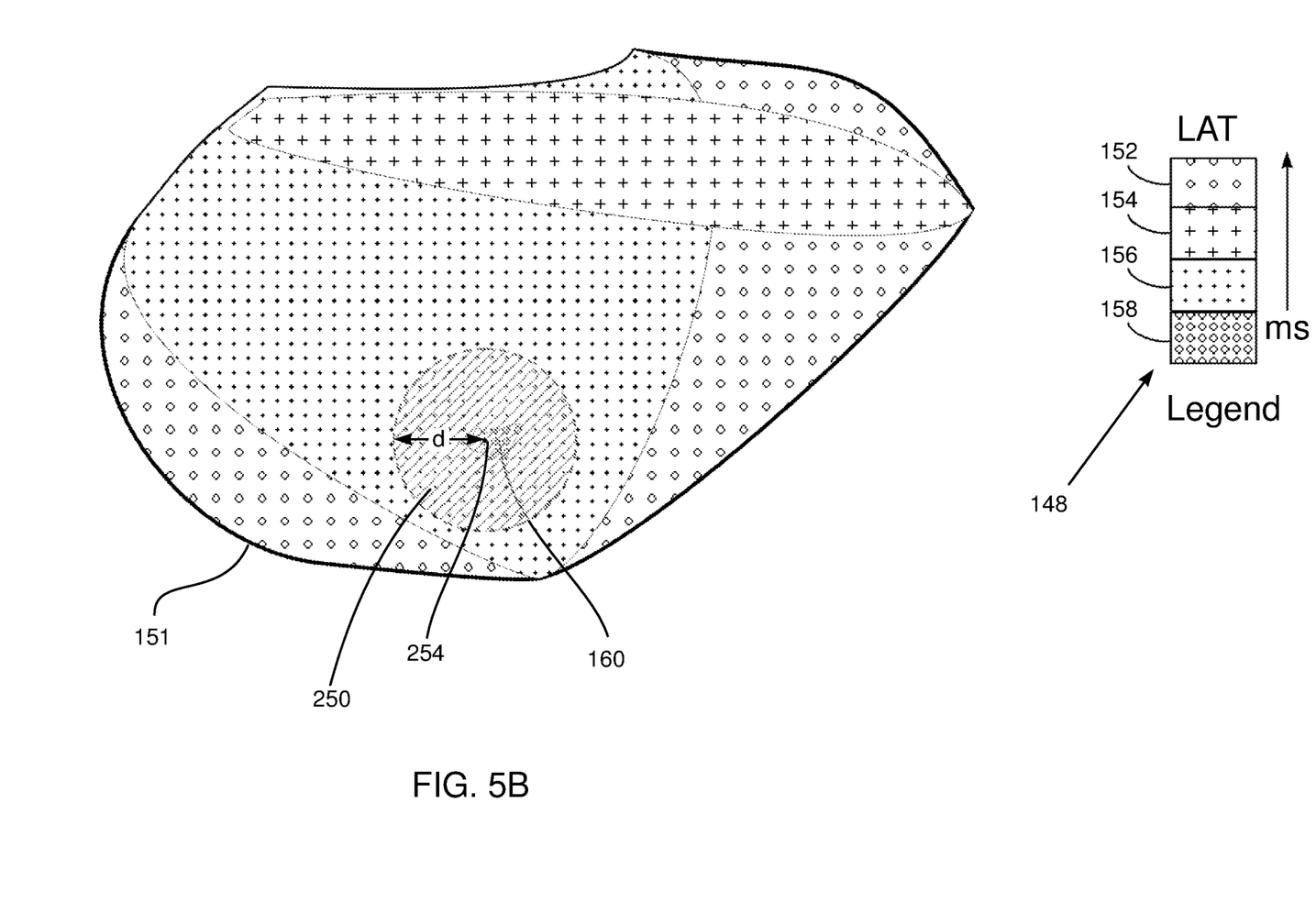

FIG. 5A is a flowchart of steps of an algorithm implemented by processor 40 and operator 22, and FIG. 5B is a schematic illustration of a map 151 explaining some of the steps, according to an embodiment of the present invention. Apart from the differences described below, map 151 is generally similar to map 150, both maps illustrating the same portion of map 49, so that elements indicated by the same reference numerals in both maps 150 and 151 are generally similar.

The following description of the algorithm assumes a retrospective review of map 150 (FIG. 4), but the description may be adapted, *mutatis mutandis*, to include real-time or near real-time production and review of the map. The algorithm enables operator 22 to form an electrophysiological assessment of heart 34.

In an initial step 188, electroanatomical map 49 of an atrium of heart 34 is produced, substantially as described above with reference to FIG. 3 and FIG. 4. The production comprises, inter alia, acquisition of IC ECG signals from identified locations of the atrium surface, and generation and display of map 49. The description below uses map 150 as a portion of map 49.

In a review step 189, operator 22 reviews map 150 and decides to inspect one or more regions of the map. In the review, the operator typically defines a distance, described in detail with respect to step 198 below, used by the processor for further analysis of the signals used to produce the map. The following descriptions of the steps of the flowchart are iterated for each region of the map inspected, and the iterated steps are illustrated as being within a rectangle 190.

In a selection step 191, operator 22 selects a region, herein assumed to comprise region 160, to review. On selection, operator 22 is presented, on display 48, with one or more IC ECG signals that processor 40 has used to generate the LAT values for the region. As explained above, for any given map region the processor may use interpolation to generate the LAT value for the region, in which case the IC ECG signals used for the interpolation are presented on display 48.

In a double-potential step 196, the operator inspects the presented IC ECG signals. Typically, processor 40 superimposes on each presented signal the annotation which the processor has selected as a valid annotation for the LAT of the signal, generally as illustrated in FIG. 3. In addition, for a double-potential signal the processor provides an indication to the operator that the signal is a double-potential signal. The indication may be by any convenient means, such as superimposing on the signal, for example as a blinking circle or a differently colored circle, the annotation that the processor did not select as the LAT of the signal, i.e., the annotation that the processor has assumed is invalid.

In a selection step 198 the operator chooses which of the two annotations of the double-potential signal is correct. In implementing the choice, the operator either validates the annotation that the processor has selected as the valid annotation, or validates the other annotation of the signal, i.e., the annotation not selected by the processor. Operator 22 typically uses controls 38 for the validation, such as by clicking on the valid annotation. On validation, processor 40 also records the location in map 150 from where the double-potential signal was acquired.

As illustrated schematically in FIG. 5B, the processor then registers in memory 44 a zone 250 of map 150 that comprises points within a predefined distance "d" of the recorded location, herein assumed to correspond to a zone-origin point 254 on the map. Distance d may be defined by operator 22, for example in review step 189. In one embodiment the predefined distance d is set at 5 mm.

In a decision step 200, the processor analyzes all the IC ECG signals that have been acquired for locations in zone 250, and determines from the analysis which signals comprise double-potential signals.

If the decision in step 200 returns positive, i.e., there is a double-potential signal in zone 250, then in a re-evaluation step 204, the processor selects the signal and re-evaluates the annotation of the selected signal in response to the annotation chosen by the operator in step 198. The re-evaluation comprises the processor propagating the validation choice performed by the operator in selection step 198 to double-potential signals in zone 250.

Thus, if the operator in step 198 validated the processor-selected choice, then in re-valuation step 204 the processor does not change the processor-selected annotations of the double potentials in zone 250. In addition, for double-potential signals outside zone 250, the processor does not change the processor-selected annotations of these double potentials.

If the operator in step 198 validated the other annotation of the signal, i.e., the operator changed the annotation selected by the processor, then in re-valuation step 204 the processor propagates the change to the double potentials in zone 250. I.e., the processor changes the annotations from those initially selected by the processor to the other annotation. In addition, for a double-potential signal outside zone 250, the processor typically annotates the peak of the signal that is closest in time to the nearest single potential signal annotation.

If the decision returns negative, i.e., there are no double-potential signals in zone 250, or all the double-potential signals in the zone have been analyzed in step 204, the flowchart proceeds to a final step 208.

In step 208, processor uses all the valid annotations that have been calculated in step 198, where the operator selects the valid annotation, and in step 204, where the processor selects the valid annotation, to update electroanatomical map 49

The description above assumes that the annotation of the P-wave is at the time of the maximum of the P-wave. The description may be changed, mutatis mutandis, to accommodate cases where the annotation of the P-wave is at other positions known in the art, such as at the time of the most negative $$\frac{dV}{dt}$$

of the P-wave.

For clarity, the description above assumes that double-potential signals are acquired from an atrium of a heart, and are analyzed according to the algorithm of FIG. 5A. The description above, mutatis mutandis, also applies to double-potential signals generated in a ventricle of the heart. Thus, embodiments of the present invention comprise analysis of double-potential signals generated in any chamber of the heart.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method for electrophysiological assessment, comprising:

acquiring electrical signals from myocardial tissue at multiple locations in a chamber of a heart;

automatically deriving from the electrical signals, by a computer processor, respective annotations, which are indicative of times within a cycle of the heart at which a conduction wave in the myocardial tissue traversed the locations;

receiving an input from a user of the computer processor indicating, for a first location in the tissue where the electrical signals comprise a double-potential signal having a first annotation and a second annotation at different respective times within the cycle of the heart, a selection of the first annotation as a valid annotation;

setting a predefined distance from the first location in response to the selection of the first annotation for the first location in the tissue; wherein the predefined distance is defined by the user;

automatically identifying, by the computer processor, one or more second locations, within the predefined distance from the first location, where the electrical signals comprise double-potential signals, each having two respective annotations;

automatically selecting, by the computer processor, in response to the selection of the first annotation, one of the two respective annotations as the valid annotation at each of the one or more second locations; and displaying the valid annotations on an electroanatomical map of the heart.

2. The method according to claim 1, wherein the chamber comprises an atrium of the heart.

3. The method according to claim 1, wherein the chamber comprises a ventricle of the heart.

4. The method according to claim 1, wherein the respective annotations comprise respective maximum voltages of a P-wave of the heart.

5. The method according to claim 1, wherein the respective annotations comprise respective most negative $$\frac{dV}{dt}s$$

of a P-wave of the heart.

6. The method according to claim 1, wherein the respective annotations comprise respective steepest negative slopes of a QRS complex of the heart.

7. The method according to claim 1, wherein prior to the selection of the first annotation as the valid annotation by the user, the computer processor provides an indication to the user that the first annotation is the valid annotation.

8. The method according to claim 1, wherein prior to the selection of the first annotation as the valid annotation by the user, the computer processor provides an indication to the user that the second annotation is the valid annotation.

9. The method according to claim 1, wherein prior to the selection of the first annotation as the valid annotation by the user, for a given second location the computer processor selects the one of the two respective annotations as an invalid annotation.

10. The method according to claim 1, wherein prior to the selection of the first annotation as the valid annotation by the user, for a given second location the computer processor selects the one of the two respective annotations as the valid annotation.

11. The method according to claim 1, wherein displaying the valid annotations comprises calculating respective local activation times (LATs) for the first location and the one or more second locations, and incorporating the LATs into the electroanatomical map of the heart.

12. Apparatus for electrophysiological assessment, comprising:
a probe configured to acquire electrical signals from myocardial tissue at multiple locations in a chamber of a heart; and
a computer processor configured to:
automatically derive from the electrical signals, respective annotations, which are indicative of times within a cycle of the heart at which a conduction wave in the myocardial tissue traversed the locations,
set a predefined distance from the first location in response to the selection of the first annotation for the first location in the tissue; wherein the predefined distance is defined by the user,
receive an input from a user of the computer processor indicating, for a first location in the tissue where the electrical signals comprise a double-potential signal having a first annotation and a second annotation at different respective times within the cycle of the heart, a selection of the first annotation as a valid annotation,
automatically identify, one or more second locations, within the predefined distance from the first location, where the electrical signals comprise double-potential signals, each having two respective annotations,
automatically select, in response to the selection of the first annotation, one of the two respective annotations as the valid annotation at each of the one or more second locations, and
display the valid annotations on an electroanatomical map of the heart.

13. The apparatus according to claim 12, wherein the chamber comprises an atrium of the heart.

14. The apparatus according to claim 12, wherein the chamber comprises a ventricle of the heart.

15. The apparatus according to claim 12, wherein the respective annotations comprise respective maximum voltages of a P-wave of the heart.

16. The apparatus according to claim 12, wherein the respective annotations comprise respective most negative $$\frac{dV}{dt}s$$

of a P-wave of the heart.

17. The apparatus according to claim 12, wherein the respective annotations comprise respective steepest negative slopes of a QRS complex of the heart.

18. The apparatus according to claim 12, wherein prior to the selection of the first annotation as the valid annotation by the user, the computer processor provides an indication to the user that the first annotation is the valid annotation.

19. The apparatus according to claim 12, wherein prior to the selection of the first annotation as the valid annotation by the user, the computer processor provides an indication to the user that the second annotation is the valid annotation.

20. The apparatus according to claim 12, wherein prior to the selection of the first annotation as the valid annotation by the user, for a given second location the computer processor selects the one of the two respective annotations as an invalid annotation.

21. The apparatus according to claim 12, wherein prior to the selection of the first annotation as the valid annotation by the user, for a given second location the computer processor selects the one of the two respective annotations as the valid annotation.

22. The apparatus according to claim 12, wherein displaying the valid annotations comprises calculating respective local activation times (LATs) for the first location and the one or more second locations, and incorporating the LATs into the electroanatomical map of the heart.

* * * * *